United States Patent [19]

Kimble et al.

[11] Patent Number: 4,654,460

[45] Date of Patent: Mar. 31, 1987

[54] METHANE CONVERSION

[75] Inventors: James B. Kimble, Bartlesville; John H. Kolts, Ochelata, both of Okla.

[73] Assignee: Phillips Petroleum Company, Bartlesville, Okla.

[21] Appl. No.: 742,338

[22] Filed: Jun. 7, 1985

[51] Int. Cl.$^4$ .............................................. C07C 2/00
[52] U.S. Cl. ..................... 585/500; 585/415; 585/417; 585/418; 585/654; 585/656; 585/657; 585/658; 585/661; 585/943
[58] Field of Search ............... 585/415, 417, 418, 500, 585/654, 656, 657, 658, 661, 943

[56] References Cited

U.S. PATENT DOCUMENTS

| | | | |
|---|---|---|---|
| 1,801,382 | 4/1931 | Wietzel | 585/943 |
| 1,863,212 | 6/1932 | Winkler | 585/415 |
| 1,987,092 | 1/1935 | Winkler | 585/417 |
| 2,123,799 | 7/1938 | Poolblelniak | 585/417 |
| 2,396,697 | 3/1946 | Gorin | 585/415 |
| 2,467,551 | 4/1949 | Gorin | 585/943 |
| 4,239,658 | 12/1980 | Mitchell, III et al. | 585/417 |
| 4,497,970 | 2/1985 | Young | 585/415 |
| 4,513,164 | 4/1985 | Olah | 585/943 |
| 4,523,049 | 6/1985 | Jones et al. | 585/541 |
| 4,523,050 | 6/1985 | Jones et al. | 585/943 |

FOREIGN PATENT DOCUMENTS 3237079 4/1984 Fed. Rep. of Germany ...... 585/500

*Primary Examiner*—William R. Dixon, Jr.
*Assistant Examiner*—Cynthia A. Prezlock
*Attorney, Agent, or Firm*—C. F. Steininger

[57] ABSTRACT

Methane is converted to higher hydrocarbons, paticularly ethylene and ethane, and most desirably ethylene, by:

contacting a feed comprising methane, such as natural gas, and a free oxygen containing gas, such as oxygen or air, with a solid contact material, comprising:

(a) a component comprising: at least one metal selected from the group consisting of Group IA and Group IIA metals;

(b) a component comprising: at least one material selected from the group consisting of phosphate radicals and compounds containing phosphate radicals; and (c), optionally, at least one material selected from the group consisting of halogen ions and compounds containing halogen ions, under oxidative conversion conditions sufficient to convert the methane to the higher hydrocarbons.

12 Claims, No Drawings

METHANE CONVERSION

The present invention relates to methane conversion. In a more specific aspect, the present invention relates to methane conversion to higher hydrocarbons. In a still more specific aspect, the present invention relates to methane conversion to ethylene and ethane.

BACKGROUND OF THE INVENTION

Olefins, such as ethylene and propylene, have become major feedstocks in the organic chemical and petrochemical industries. Of these, ethylene is by far the more important chemical feedstock, since the requirements for ethylene feedstocks are about double those for propylene feedstocks. Consequently, feedstocks for the production of ethylene are in relatively short supply.

Numerous suggestions have been made for the production of ethylene from various feedstocks by a variety of processes.

At the present time, ethylene is produced almost exclusively by dehydrogenation or pyrolysis of ethane and propane, naptha and, in some instances, gas oils. About 75% of the ethylene is produced by steam cracking of ethane and propane derived from natural gas. However, natural gas contains as little as 5 volume percent and, in rare instances, as much as 60 volume percent of hydrocarbons other than methane, the majority of which is ethane. However, typical natural gases contain less than about 12 to 15% of ethane. In addition to the relatively small quantities of ethane and propane available for use, separation of these components from natural gas is itself an expensive and complex process, usually involving compression and expansion, cryogenic techniques and combinations thereof.

It would, therefore, be highly desirable to be able to produce ethylene from the much more abundant methane. However, methane's high molecular stability, compared to other aliphatics, makes its use in ethylene production difficult and no significant amount of ethylene is produced commercially from methane at the present time.

Pyrolytic or dehydrogenative conversion of methane or natural gas to higher hydrocarbons has been proposed. However, relatively severe conditions, particularly temperatures in excess of 1000° C., are required. In addition, such reactions are highly endothermic and thus energy intensive. In order to reduce the severity of the conditions, particularly temperature, numerous proposals to catalyze pyrolytic reactions have been made. Some of these processes do, in fact, reduce the required temperatures, but the conversion of methane and the selectivity to ethylene are still quite low.

Another promising approach is the oxidative conversion of methane or natural gas to higher hydrocarbons. However, these techniques are still in the developmental stage and experimentation is hampered by differences of opinion and lack of a complete understanding of the process. For example, most workers in the art refer to the process as "oxidative coupling". However, there is little agreement with regard to the function performed by the oxygen and how this function is performed. Accordingly, the terminology, "oxidative coupling", will be avoided herein, and the present process, irrespective of the function of the oxygen or of the manner in which it performs its function, will be referred to as "oxidative conversion of methane". In such processes, it is conventional to contact the methane with solid materials. The nature of these contact materials, the function thereof and the manner in which such function is performed are also subject to diverse theories. For example, workers in the art refer to the function of the contact material as a purely physical phenomenon, in some cases as adsorption-desorption, either of atomic or molecular oxygen and either on the surface or occluded within the solid material, oxidation-reduction utilizing multivalent metals capable of oxidation-reduction, adsorption and desorption of the hydrocarbons on the solid materials, a free radical mechanism, etc. Consequently, the solid materials, utilized in the process, are referred to as "contact materials", "promoters", "activators" and "catalysts". Accordingly, in order to avoid functional categorization, the terms "solid contact material" or "solid contact materials" will be utilized in the present application.

Based on the prior art, oxidative conversion of methane results in the formation of a variety of products. The most readily produced products are carbon dioxide, carbon monoxide and/or water and methanol, formaldehyde and other oxygenated hydrocarbons in combination with one or more of carbon dioxide, carbon monoxide and water. Higher hydrocarbons, particularly ethylene and ethane, are either not formed or are formed in such small quantitites that commercially viable processes have not been developed to date. Along with poor selectivity to higher hydrocarbons, particularly ethylene and ethane and still more particularly to ethylene, such processes also result in low conversions of the methane feed.

It is clear from the above that the suitability of particular contact materials is unpredictable. In addition to being dependent upon the type of contact material, the conversion of methane and selectivity to particular products also depends upon the conditions and the manner in which the reaction is carried out, and there is also little basis for predicting what conditions or what mode of operation will result in high conversions and selectivity to particular products.

SUMMARY OF THE INVENTION

It is therefore, an object of the present invention to provide an improved method for the conversion of methane. Another and further object is to provide an improved method for the oxidative conversion of methane. Yet another object is to provide a method for the oxidative conversion of methane at improved conversion levels. Another and further object of the present invention is to provide a method for the oxidative conversion of methane, which results in improved selectivity to higher hydrocarbons. A further object of the present invention is to provide a method for the oxidative conversion of methane, which results in improved conversion and selectivity to higher hydrocarbons. A still further object of the present invention is to provide a method for the oxidative conversion of methane, which results in improved selectivity to ethylene and ethane. Yet another object of the present invention is to provide a method for the oxidative conversion of methane, which results in improved conversion and selectivity to ethylene and ethane. Another object of the present invention is to provide a method for the oxidative conversion of methane, which results in improved selectivity to ethylene. Another and further object of the present invention is to provide a method for the oxidative conversion of methane, which results in improved conversion and selectivity to ethylene. A further object of the present invention is to provide a method for the oxidative conversion of methane, which can be carried out utilizing inexpensive starting materials. Another object of the present invention is to provide a method for the oxidative conversion of methane, which can be carried out under relatively mild conditions. A still further object of the present invention is to provide a method for the oxidative conversion of methane utilizing an improved contact material.

These and other objects and advantages of the present invention will be apparent from the following description.

In accordance with the present invention, methane is converted to higher hydrocarbons, particularly ethylene and ethane, by:

contacting a feed comprising methane and a free oxygen containing gas with a solid contact material, comprising:

(a) a component comprising: at least one metal selected from the group consisting of Group IA and Group IIA metals;

(b) a component comprising: at least one material selected from the group consisting of phosphate radicals and compounds containing phosphate radicals; and (c), optionally, at least one material selected from the group consisting of halogen ions and compounds containing halogen ions, under oxidative conversion conditions sufficient to convert said methane to said higher hydrocarbons.

DETAILED DESCRIPTION

The present invention is based on the discovery that methane can be converted to higher hydrocarbons, particularly ethylene and ethane and more particularly to ethylene, by:

contacting a feed comprising methane and a free oxygen containing gas with a solid contact material, comprising:

(a) a component comprising: at least one metal selected from the group consisting of Group IA and Group IIA metals;

(b) a component comprising: at least one material selected from the group consisting of phosphate radicals and compounds containing phosphate radicals; and (c) optionally, at least one material selected from the group consisting of halogen ions and compounds containing halogen ions, under oxidative conversion conditions sufficient to convert said methane to said higher hydrocarbons.

Preferred Group IA metals include at least one metal selected from the group consisting of lithium, sodium, and potassium.

Preferred Group IIA metals include at least one metal selected from the group consisting of magnesium, calcium, strontium and barium.

In those instances in which Group IA metals alone and Group IIA metals alone are utilized, in combination with phosphate radicals, the contact material will comprise predominantly Group IA metal phosphates and Group IIA metal phosphates, respectively. Where both Group IA metals and Group IIA metals are utilized with phosphate radicals, the exact nature of the contact materials is not fully known. It is believed that the Group IA metals are predominantly in their carbonate or oxide form and that the oxides are converted to carbonates during the course of the oxidative conversion of methane to higher hydrocarbons in the presence of a free oxygen-containing gas. The Group IIA metals are believed to be in the form of Group IIA metal phosphates. However, it is also possible that mixtures of Group IA and Group IIA phosphates are present, such mixtures of phosphates in combination with Group IA metal oxides and/or carbonates or in combinations with mixtures of Group IA and Group IIA metal oxides and/or carbonates. The phosphate radicals may also be in the form of other metal phosphates in combination with Group IA and/or Group IIA metals with Group IA metal and/or Group IIA metals present predominantly in their oxide and/or carbonate form.

Accordingly, it is to be understood that the present invention is not to be limited to any particular theory concerning the form of the components of the contact material, so long as the specified components, i.e., Group IA and/or Group IIA metals and phosphate radicals are present.

The presence of a halogen, preferably chlorine, has been found to be highly beneficial, both in increasing the conversion of methane and the selectivity to higher hydrocarbons, particularly ethylene and ethane and more particularly to ethylene. The halogen may be incorporated in the contact material itself during the preparation. However, in some cases, it is difficult to incorporate sufficient halogen, to be effective, in the contact material itself. Consequently, it is more convenient to prepare the solid contact material with or without the halogen present and to, thereafter, pretreat the contact material with a material containing at least one halogen, preferably in the reaction zone in which the reaction is to be carried out, prior to the introduction of the feed comprising methane and free oxygen containing gas. Suitable materials containing halogens, in the vapor or gaseous state, include chlorine gas, methyl chloride, methylene chloride and corresponding gaseous or vaporous materials containing other halogens such as iodine, bromine, etc. It is not known exactly what form the halogen is in, either when incorporated in the contact material itself or added by pretreatment of the contact material. However, it is believed that the halogen is present in the contact material, in either case, on or near the surface of the contact material particles. As a result, it has been observed that the halogen content of the contact material decreases over a period of time. Consequently, as an alternative to or in addition to incorporating the halogen in the contact material or pretreating the contact material with a halogen-containing material, the halogen-containing material may be, at least intervally, added as the reaction proceeds, i.e., either continuously adding a small amount of the halogen-containing material to the feed materials or at necessary intervals throughout the conduct of the reaction. In the latter case, the halogen-containing material may be added to the feed materials intervally or the flow of feed materials may be discontinued, the halogen-containing material added and the flow of feed materials thereafter resumed.

The contact materials of the present invention have been found to be long lived and little or no deactivation appears to occur when these contact materials are utilized for the conversion of methane in the presence of a free oxygen containing gas. Consequently, the method of the present invention has the distinct advantage that it can be carried out in an essentially continuous manner, with the possible exception of at least intervally replenishing the halogen content of a contact material in which the halogen has been incorporated during the preparation of the contact material or by pretreatment of the contact material. This is in clear contrast to most prior art techniques which carry out the oxidative conversion of methane in a cyclic manner, particularly those processes utilizing contact materials containing a multivalent metal compound capable of undergoing oxidation and reduction. The many disadvantages of such cyclic operation are evident from the fact that rapid cycling is necessary. For example, methane feed is passed through the contact material for a few minutes, feed is discontinued and the contact material is usually purged with an inert gas, such as nitrogen, thereafter, the contact material is reoxidized by contact with a free oxygen containing gas, a second purge with inert gas is often utilized and, finally, the methane feed is resumed. In many cases, the reoxidation or regeneration with a free oxygen containing gas requires a longer period of time than the actual contact time with methane for the main reaction. In any event, such short time cyling and the short time of actual conduct of the reaction are distinct disadvantages.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are often products of the process. It has also been found that inert gases, such as nitrogen, helium and the like are not detrimental. Consequently, the method of the present invention can effectively utilize any conventional natural gas.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent" gas is meant to include any gaseous or vaporous material, present in the methane-containing gas, the free oxygen containing gas or in the form of an added gas or vapor, which is essentially inert with respect to the oxidative conversion of methane and, thus, does not significantly decrease the conversion of methane and/or the selectivity to the production of higher hydrocarbons. Suitable diluents include, nitrogen, helium, steam etc.

The relative proportions of the components of the contact material do not appear to be particularly critical. Accordingly, any amounts of the individual components may be present so long as effective amounts of the other components are present. The term "effective amount" is used herein to identify the quantity of a component which, when present in the contact material, results in a significant increase the conversion of methane and/or the selectivity to higher hydrocarbons, particularly ethylene and ethane, compared with a contact material without the component in question. Where the contact material is in the form of a Group IA or Group IIA metal phosphate, the proportions will obviously be the atomic proportions necessary to form electrically balanced phosphates of the Group IA or Group IIA metal. Where both Group IA and Group IIA metals are present, the Group IIA metal is preferably present in an amount sufficient to provide the desired electrically balanced Group IIA metal phosphate. As indicated previously, it is possible that some of the Group IA metal may also be in the form of a Group IA metal phosphate. However, in these combinations, the most desirable contact material contains what may be termed "excess" or "free" Group IA metals in addition to or in excess of any amount which may be present in electrically neutral compounds of Group IA metal phosphates or, to the extent no Group IA metal phosphates are present, all of the Group IA metal will be in the form of free or excess Group IA metals. This free or excess Group IA metal is believed to be in the form of oxides or carbonates of the metal. Usually, the free or excess Group IA metal will be present in amounts from about 0.1 wt. percent to about 50 wt. percent (depending upon the atomic weight of the element), expressed in terms of elemental metal, based on the total weight of the contact material. Preferred ranges of Group IA metals are between about 0.5 wt. percent and about 15 wt. percent and, still more preferably, between about 1 wt. percent and about 5 wt. percent. When the phosphates are present as phosphates of metals other than a Group IIA metal, the same criteria apply, i.e., the above-mentioned amounts of the Group IA metal is present as free or excess Group IA metal and the Group IIA metals are also present in similar amounts. A halogen, when present, is utilized in amounts from an effective amount to near 100 wt. percent, usually between about 0.1 wt. percent and about 5 wt. percent, expressed as elemental halogen based on the total weight of the composition of the contact material.

The contact materials can be prepared by any suitable method known in the art for the preparation of such mixtures in a solid form. Conventional methods include coprecipitation from an aqueous, an organic or a combination solution-dispersion, impregnation, dry mixing, wet mixing or the like, alone or in various combinations. In general, any method can be utilized which provides contact materials containing the prescribed components in effective amounts. Obviously, Group IA or Group IIA metal phosphates are commercially available and can be utilized as such. However, it is preferred that such commercial materials be calcined, for example at about 700° F. to about 1200° F. for from 1 to 24 hours, in order to remove water of hydration or water which would be vaporized during the conduct of the oxidative conversion process. Standard coprecipitation techniques may be utilized to prepare contact materials containing Group IA and Group IIA metals or Group IA and/or Group IIA and metals other than Group IIA metals. Such coprecipitation should also be followed by suitable calcination in the presence of free oxygen containing gas. An alternative procedure would be to form a slurry of suitable compounds of the components in a sufficient water or other carrier to form a thick slurry, dry the slurry, usually at a temperature sufficient to volatilize the water or other carrier, such as 220° F. to about 450° F., and, thereafter, calcine the material in the presence of a free oxygen containing gas.

Any suitable compounds of the components may be utilized, for example, acetates, halides, nitrates, carbonates, oxides, hydroxides, phosphates and the like.

In the present invention, it has been found that the method can be carried out between two extremes, namely, low conversion of methane/high selectivity to higher hydrocarbons, particularly ethylene, and high conversion of methane/low selectivity to the higher hydrocarbons, particularly ethylene. The process parameters (space velocity, temperature, and reactant partial pressure) can, to some extent, be used to control the reaction at the desired point between these two limits. Consequently, the reaction conditions may vary between broad limits.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

The lithium phosphate of the examples is a commercially available lithium phosphate. The $Li/Fe_3(PO_4)_2$ was prepared by mixing 0.25 mole of ferric nitrate in 50 cc of water, mixing 0.73 mole of 85% phosphoric acid in 70 cc of water, combining the two mixtures and adding 0.07 mole of lithium nitrate. The mixture was then heated to reduce the volume to about 140 milliliters. Thereafter, the filtered product was calcined at 650° C. for 24 hours. The resultant contact material had a ratio of Li/Fe/P of 0.3/1/3. The copper phosphate and the aluminum-zirconium-copper/$PO_4$ were prepared by standard coprecipitation procedures, using copper, aluminum and zirconium nitrates and ammonium or diammonium phosphate. The pH was adjusted, where necessary to form a gel, with ammonium hydroxide. The gelled material was filtered and thereafter calcined in the presence of the free oxygen containing gas.

The contact material was loaded in a quartz reactor having a thermocouple well centered in the contact material bed. The reactor was brought up to temperature under nitrogen or air and, thereafter, methane and air flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography.

The variables and results of this series of tests are set forth in the Table below. Conversion is mole percent of methane converted. Selectivity is based on mole percent of methane feed converted to a particular product. The CHs rate can be expressed as cc/min/cc of contact material. For example, when 70 cc/min of $CH_4$ was fed to a reactor containing 25 cc of catalyst the flow rate would be 2.8 cc/min of $CH_4$/cc of contact material. The volumetric ratio of $CH_4$ to air is given in terms of cc/min of $CH_4$ per cc/min of air present.

TABLE

| Run No. | Contact Material | Volume $CH_4$/Air | Volume of Con. Mat. | Sample Time (min) | Temp (°C.) | Conversion | Selectivity % | | | | | | |
|---|---|---|---|---|---|---|---|---|---|---|---|---|---|
| | | | | | | | $C_2=$ | $C_2$ | $C_2$'s | $C_3=$ | $C_3$ | $CO_2$ | CO |
| 1 | $Li_3PO_4$ | 104/104 | 25 cc | 14 | 706.0 | 3.5 | 4.2 | 19.3 | 23.5 | 0.0 | 0.0 | 45.3 | 31.2 |
| | | | | 97 | 700.0 | 2.9 | 0.0 | 17.9 | 17.9 | 0.0 | 0.0 | 48.1 | 34.0 |
| | | | | 132 | 700.0 | 2.9 | 3.4 | 16.6 | 20.0 | 0.0 | 0.0 | 46.3 | 33.7 |
| | | | | 162 | 754.0 | 7.9 | 14.2 | 22.0 | 36.2 | 0.0 | 0.0 | 40.3 | 23.5 |
| | | | | 208 | 752.0 | 7.4 | 13.2 | 21.5 | 34.7 | 0.0 | 0.0 | 40.7 | 24.6 |
| 2 | $Li/Fe_3(PO_4)_2$ | 104/104 | 25 cc | 10 | 702.2 | 0.1 | 0.0 | 0.0 | 0.0 | 0.0 | 0.0 | 0.0 | 100.0 |
| | | | | 49 | 704.0 | 0.0 | 0.0 | 0.0 | 0.0 | 0.0 | 0.0 | 0.0 | 0.0 |
| | | | | 94 | 753.0 | 0.5 | 0.0 | 29.1 | 29.1 | 0.0 | 0.0 | 0.0 | 70.9 |
| | | | | 132 | 751.0 | 0.5 | 0.0 | 29.2 | 29.2 | 0.0 | 0.0 | 0.0 | 70.8 |
| | | | | 202 | 797.0 | 2.1 | 6.1 | 21.6 | 27.7 | 0.0 | 0.0 | 0.0 | 72.2 |
| | | | | 236 | 802.0 | 2.4 | 6.8 | 19.0 | 25.8 | 0.0 | 0.0 | 3.7 | 70.4 |
| | | | | 306 | 801.0 | 2.3 | 6.2 | 19.1 | 25.3 | 0.0 | 0.0 | 3.8 | 70.9 |
| | | | | 336 | 801.0 | 2.2 | 6.2 | 18.5 | 24.7 | 0.0 | 0.0 | 3.9 | 71.4 |
| 3 | $Cu_2(P_2O_7)$ | 70/80 | 25 cc | 40 | 750.0 | 0.8 | — | 20.0 | 20.0 | — | — | 20.0 | 60.0 |
| 4 | Al—Zr—Cu/$PO_4$ | 70/80 | 25 cc | 40 | 700.0 | 13.0 | — | — | — | — | — | 50.0 | 50.0 |

It has also been found that the production of $CO_2$ was high and, hence, the HC selectivity was low, if the concentration of $O_2$ in the initial feed stream is high. Accordingly, the HC selectivity can be increased and the $CO_2$ production concomittantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

What is claimed is:

1. A method for the oxidative conversion of methane to higher hydrocarbons, comprising:
   contacting a feed material comprising methane and a free oxygen-containing gas with a solid contact material selected from the group consisting of:
   (a) a contact material consisting essentially of: (1) at least one material selected from the group consisting of Group IA metals, Group IIA metals and compounds thereof and (2) at least one material selected from the group consisting of phosphate radicals and compounds containing phosphate radicals, and
   (b) a contact material consisting essentially of: (1) at least one material selected from the group consisting of Group IA metals, Group IIA metals and compounds thereof, (2) at least one material selected from the group consisting of phosphate radicals and compounds containing phosphate radicals and (3) at least one material selected from the group consisting of halogen ions and compounds containing halogen ions under oxidative conversion conditions sufficient to convert said methane to higher hydrocarbons.

2. A method in accordance with claim 1 wherein the feed is natural gas.

3. A method in accordance with claim 1 the Group IA metal is a metal selected from the group consisting of lithium, sodium and potassium.

4. A method in accordance with claim 1 wherein the Group IIA metal is a metal selected from the group consisting of magnesium, calcium strontium and barium.

5. A method in accordance with claim 1 wherein the method is carried out in an essentially continuous manner.

6. A method in accordance with claim 1 wherein the volumetric ratio of methane to free oxygen is at least about 1/1.

7. A method in accordance with claim 1 wherein the volumetric ratio of methane to free oxygen is between about 1/1 and about 30/1.

8. A method in accordance with claim 1 wherein the temperature of contacting is at least about 500° C.

9. A method in accordance with claim 1 wherein the temperature of contacting is between about 500° C. and about 1500° C.

10. A method in accordance with claim 1 wherein the contact material consists essentially of: (1) at least one material selected from the group consisting of Group IA metals, Group IIA metals and compounds thereof and (2) at least one material selected from the group consisting of phosphate radicals and compounds containing phosphate radicals.

11. A method in accordance with claim 1 wherein the contact material consists essentially of: (1) at least one material selected from the group consisting of Group IA metals, Group IIA metals and compounds thereof, (2) at least one material selected from the group consisting of phosphate radicals and compounds containing phosphate radicals and (3) at least one material selected from the group consisting of halogen ions and compounds containing halogen ions.

12. A method in accordance with claim 11 wherein the halogen is chlorine.

* * * * *

Notice of Adverse Decisions in Interference

In Interference No. 101,898, involving Patent No. 4,654,460, J. B. Kimble and J. H. Kolts, METHANE CONVERSION, final judgment adverse to the patentees was rendered Apr. 5, 1991, as to claims 1-12.
*(Official Gazette September 3, 1991.)*